United States Patent [19]
Niedospial et al.

[11] Patent Number: 5,653,698
[45] Date of Patent: Aug. 5, 1997

[54] COUPLING SYSTEMS FOR SAFTEY CANNULA

[75] Inventors: John J. Niedospial, Princeton Juntion, N.J.; Linn C. Hoover, Webster, N.Y.; Michael T. Mallon, New Fairfield, Conn.; James E. Hoyes, Somerset, N.J.; Robert J. DeLuccia, Mamaroneck, N.Y.

[73] Assignee: Sanofi Winthrop, Inc., New York, N.Y.

[21] Appl. No.: 588,184

[22] Filed: Jan. 18, 1996

Related U.S. Application Data

[63] Continuation-in-part of Ser. No. 372,271, Jan. 13, 1995, Pat. No. 5,501,676.

[51] Int. Cl.$^6$ ............................................. A61M 5/00
[52] U.S. Cl. ..................... 604/283; 604/86; 604/411; 604/905; 604/403; 604/414
[58] Field of Search ........................ 604/283, 82, 83, 604/86, 89, 88, 90, 91, 200, 87, 201, 412, 413, 415, 416, 411, 905, 403, 232, 280, 414

[56] References Cited

U.S. PATENT DOCUMENTS

| | | |
|---|---|---|
| 4,329,989 | 5/1982 | Dallons . |
| 4,585,445 | 4/1986 | Hadtke . |
| 4,643,724 | 2/1987 | Jobe . |
| 4,786,281 | 11/1988 | Valentini et al. ................. 604/86 |
| 4,981,469 | 1/1991 | Whitehouse et al. ............ 604/86 |
| 5,066,287 | 11/1991 | Ryan . |
| 5,171,214 | 12/1992 | Kolber et al. .................... 604/82 |
| 5,190,534 | 3/1993 | Kendell ............................ 604/4 |
| 5,226,900 | 7/1993 | Bancsi . |
| 5,389,086 | 2/1995 | Attermeier et al. ............. 604/905 |

*Primary Examiner*—Michael Powell Buiz
*Assistant Examiner*—N. Kent Gring
*Attorney, Agent, or Firm*—William J. Davis; Imre Balogh; Paul E. Dupont

[57] ABSTRACT

A coupling system for transferring fluids from a medicament-containing cartridge to an injection site comprises a fluid flow channel, a blunt cannula defining the distal end of the fluid flow channel, a needle cannula defining the proximal end of the fluid flow channel, and means for fixedly connecting the needle cannula to the blunt cannula.

6 Claims, 10 Drawing Sheets

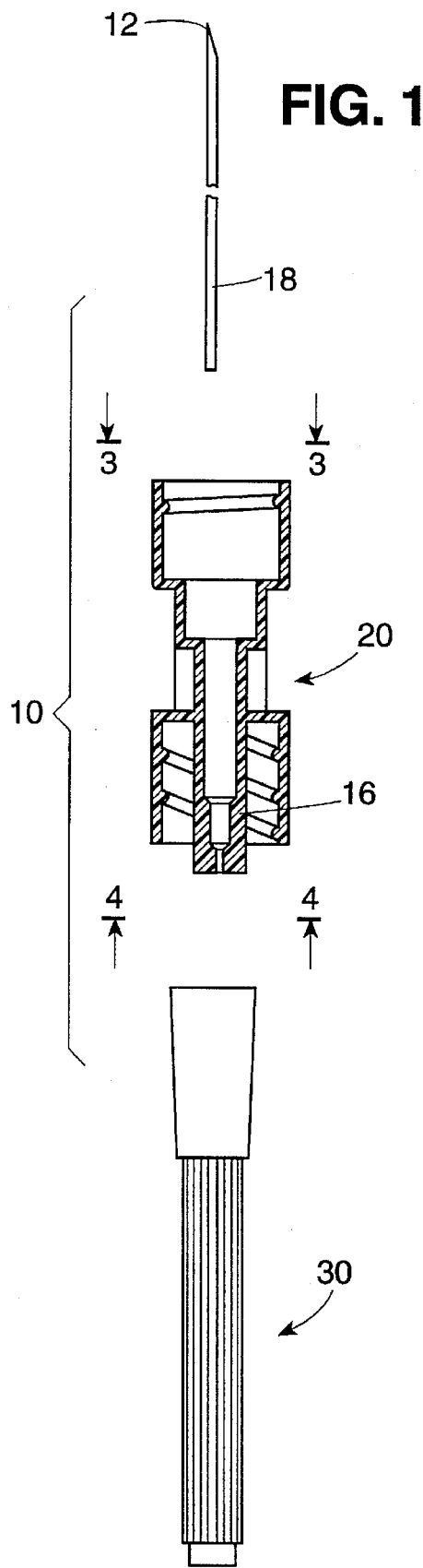
FIG. 1
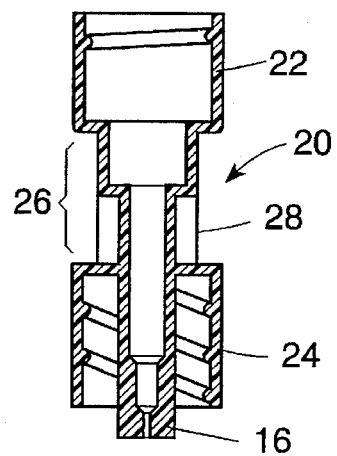
FIG. 2
FIG. 3
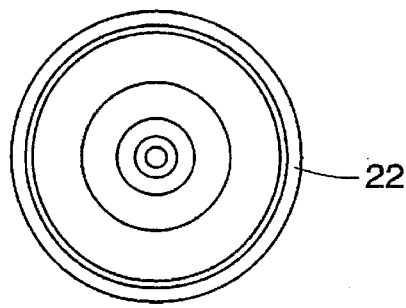
FIG. 4
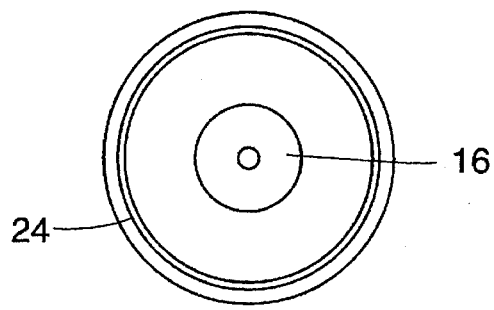

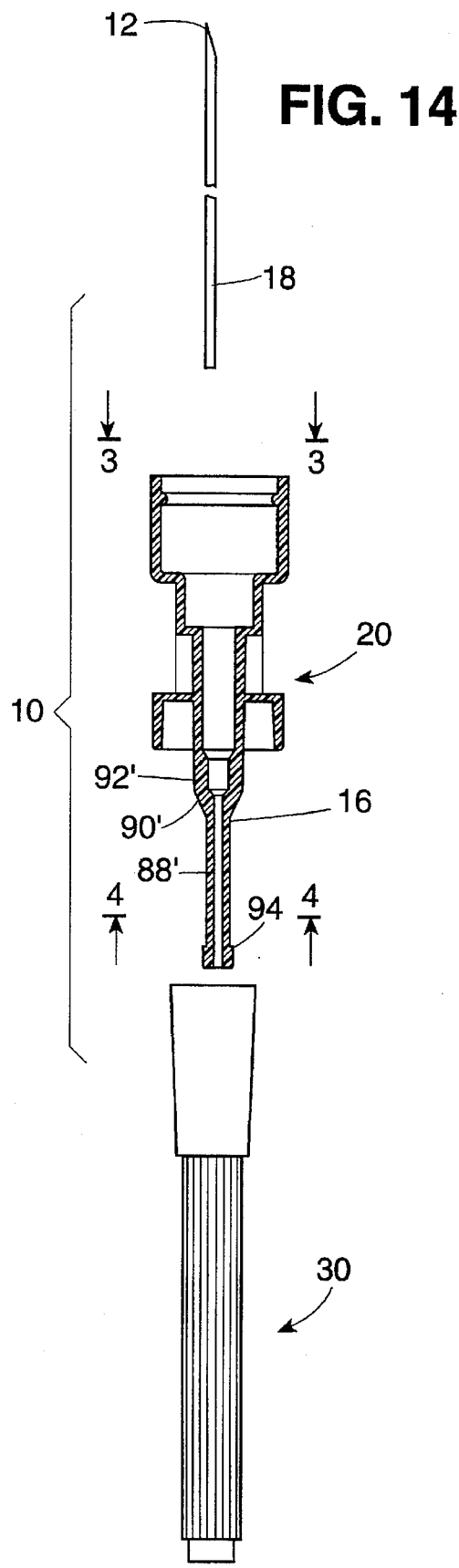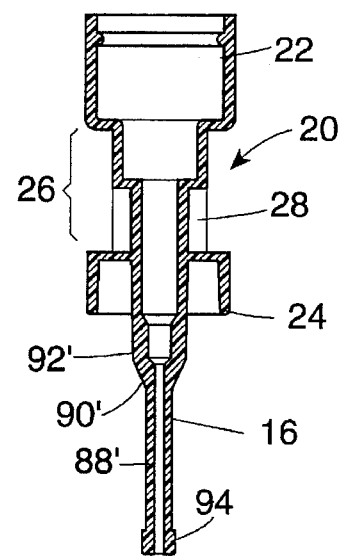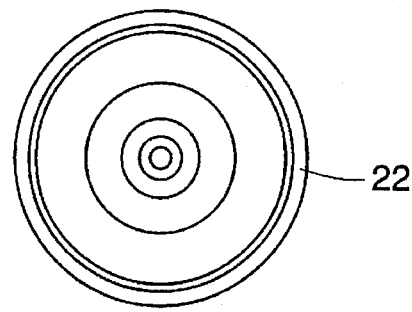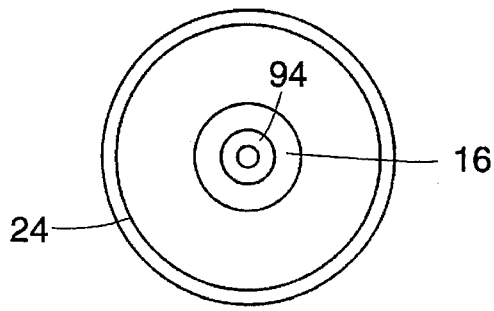

COUPLING SYSTEMS FOR SAFTEY CANNULA

This is a continuation-in-part of application Ser. No. 08/372,271 filed Jan. 13, 1995, now U.S. Pat. No. 5,501,676.

BACKGROUND OF THE INVENTION

1. Field of Invention

This invention relates to coupling systems for transferring materials from one flow conduit to another. More particularly, the invention relates to a hub/safety needle cannula designed for use in combination with medicament-containing cartridge units. Preferably, the hub/safety needle cannula and cartridge unit is used in conjunction with a cartridge holder for purpose of safety and easy handling.

2. Reported Developments

Disposable medicament-containing cartridge-needle units for use in conjunction with reusable hypodermic syringe holders are well known in the art. Such cartridges conventionally feature a cylindrical body closed at the proximal end with a flexible piston slideable within the bore of the cartridge and closed at the distal necked-down end with a diaphragm secured to the cartridge by a crimped-on metal collar. The distal necked-down end conventionally is fitted with a steel needle/needle hub unit and a needle sheath. Such needle/needle hub units have, minimally, a sharp end, typical of the type associated with hypodermic syringes.

Such cartridge-needle units can be used in conjunction with reusable syringe holders which allow the user to avoid handling the cartridge-needle unit when the needle is exposed. Nevertheless, health care workers are especially susceptible to accidental and potentially infectious, and indeed, on occasion, possibly fatal, needle strikes due to the careless handling and/or disposing of the cartridge-needle unit after use. The consequences to health care workers of strikes from needles contaminated with various infectious diseases, such as hepatitis or AIDS, can be particularly severe. The frequency of such accidental needle strikes in the United States is surprisingly great, and has been estimated to be approximately one million needle strikes per year. Moreover, the cost to health care organizations for the testing of health care workers accidentally stricken by used needles is a significant burden on health care costs. Therefore, it would be desirable to further protect health care workers by providing medicament containing cartridges without having to expose the user to the needle commonly associated with such cartridges.

In response to the need of preventing "accidental needle strike injuries", numerous devices have been developed which shield or cover the sharp needle tip. One recently developed system, as described in PCT/US89/00273, comprises a blunt cannula which is to be received by a pre-slit injection site. Commercially available under the InterLink trademark, this pre-slit injection site and blunt cannula have been adapted for intravenous administration as described in published patent applications and patents. One of the key features of this system is the elimination of traditional "sharp" needles which are used in various procedures. For example, as described in PCT/US90/01350, the blunt cannula is depicted in a press-fit combination with a syringe of known construction. Rather than using a traditional needle, the blunt cannula is attached to the syringe and then inserted through the pre-slit injection site located in an IV tubing line. The content of the syringe is then delivered into the IV line. Once the content is delivered, the cannula is withdrawn from the site and properly disposed. Hence, the administration of the syringe content, through an IV line, can now be completed without the use of standard needles that can cause accidental needle strikes.

Further, in response to the need of preventing accidental needle strike injuries the prior art has provided a conventional disposable medicament cartridge designed to receive a blunt cannula and which is usable with pre-slit injection sites. More specifically, the coupling system for transferring fluid medicament from a cartridge to a pre-slit injection site comprises:

a fluid flow channel;

a blunt cannula forming the distal end of the fluid flow channel to be received by the pre-slit injection site;

a needle cannula forming the proximal end of the fluid flow channel; and means for connecting the needle cannula to the blunt cannula.

The means for connecting the needle cannula to the blunt cannula comprises a hub having a sleeve which extends around and beyond the proximal end of the needle cannula so as to prevent accidental needle strike when the coupling system is snapped onto the fluid medicament-containing cartridge.

While this coupling system prevents accidental needle strike injuries to the health care practitioner, and as a result, greatly advances the art of delivering fluid medicaments to patients, there is still a need for improving the coupling system in relation to its use with the pre-slit sites. The connection between the pre-slit site and the coupling system should provide for a leak-proof seal, easy alignment in repeated use, sufficient holding force to prevent fall-out and proper reseal of the septum in the pre-slit site to prevent entering of airborne foreign matter into the site.

It is an object of the present invention to provide a coupling system for fluid medicaments containing cartridges from which such fluid medicaments can be delivered to an injection site without accidental needle strike to the health care professional or the patients.

It is another object of the present invention to provide a coupling system used in conjunction with a pre-slit injection site that greatly reduces or eliminates leakage, misalignment and the entering of foreign matter into the injection site.

It is still another object of the present invention to provide a more positive means of engaging and locking of the (luer) coupling system to reduce inadvertent disassembling of the cartridge from the injection site.

It is still another object of the present invention to provide a coupling system with a fluid medicament containing cartridge unit which can be used in conjunction with a cartridge holder for purpose of safety and ease of handling.

It is still another object of the present invention to provide a coupling system that is compatible with various pre-slit injection sites.

It is still another object of the present invention to provide a coupling system having a retention feature which inhibits easy or unintentional removal of the coupling system from a pre-slit injection site.

SUMMARY OF THE INVENTION

In accordance with this invention, an improved coupling system is provided for transferring fluids from a medicament-containing cartridge to an injection site which reduces the possibility of accidental needle strikes.

More specifically, the invention provides a coupling system for transferring fluid medicament from a cartridge to an injection site comprising three embodiments.

Embodiment I

There is provided a coupling system for transferring a medicament from a cartridge to a pre-slit injection site wherein said pre-slit injection site comprises:

a cylindrical housing having a first end and a second end;

internal male luer threads located in said cylindrical housing adjacent to said second end to receive and engage a catheter having female luer threads thereon;

a hollow cylindrical fluid flow member providing a sterile fluid flow coupling when said catheter is engaged with said pre-slit injection site; and a resealable septum located at the first end of said housing to seal said pre-slit injection site when said pre-slit injection site is not engaged by said catheter;

wherein said coupling system comprises:

a hub having a proximal and distal end and a flow channel located centrally therein, said flow channel comprising:

a needle cannula having a sharp end at the proximal end of the hub; and a blunt cannula at the distal end of the hub;

said hub comprising:

a first sleeve located on the proximal end of the hub and designed to engage a closure on a cartridge;

a second sleeve located on the distal end of the hub having internal threads thereon to engage said catheter connected to said pre-slit injection site; and a middle portion integral with and connecting the sleeves on the proximal and distal ends of the hub;

said first sleeve covering in a spaced relationship and extending beyond the sharp end of said needle cannula.

It is an advantageous feature of this invention that an improved coupling system is provided for commercially available medicament-containing cartridges which can be used safely and effectively without exposing the user to the needle cannula. This reduces the susceptibility of health care workers to accidental needle strikes.

When the coupling system is used in conjunction with a cartridge, the assembly comprises:

a coupling system for transferring a medicament from a cartridge to a pre-slit injection site in combination with a cartridge wherein said pre-slit injection site comprises:

a cylindrical housing having a first end and a second end;

internal male luer threads located in said cylindrical housing adjacent to said second end to receive and engage a catheter having female luer threads thereon;

a hollow cylindrical fluid flow member providing a sterile fluid flow coupling when said catheter is engaged with said pre-slit injection site; and a resealable septum located at the first end of said housing to seal said pre-slit injection site when said pre-slit injection site is not engaged by said catheter;

wherein said coupling system in combination with a cartridge comprises:

a cartridge, comprising a hollow body prefilled with a medicament having a sealed diaphragm on the distal end thereof and a piston axially and reciprocally slideable through the interior of said body; and a coupling system for transferring said medicament from said cartridge to the pre-slit injection site, said coupling system comprising:

a hub having a proximal and distal end and a flow channel located centrally therein, said flow channel comprising:

a needle cannula having a sharp end at the proximal end of the hub; and a blunt cannula at the distal end of the hub;

said hub comprises:

a first sleeve located on the proximal end of the hub and designed to engage a closure on said medicament-containing cartridge;

a second sleeve located on the distal end of the hub having internal threads thereon to engage said catheter connected to said pre-slit injection site; and a middle portion integral with and connecting the sleeves on the proximal and distal ends of the hub;

said first sleeve covering in a spaced relationship and extending beyond the sharp end of said needle cannula to prevent accidental needle strike.

The coupling system is also used in combination with a cartridge and holder assembly, the combination comprising:

(a) a pre-slit injection site;

(b) a cartridge in a cartridge holder; and (c) a coupling system;

wherein said pre-slit injection site comprises:

a cylindrical housing having a first end and a second end;

internal male luer threads located in said cylindrical housing adjacent to said second end to receive and engage a catheter having female luer threads thereon;

a hollow cylindrical fluid flow member providing a sterile fluid flow coupling when said catheter is engaged with said pre-slit injection site; and a resealable septum located at the first end of said housing to seal said pre-slit injection site when said pre-slit injection site is not engaged by said catheter;

wherein said cartridge comprises:

a hollow body prefilled with a medicament having a sealed diaphragm on the distal end thereof and a piston axially and reciprocally slideable through the interior of said body; and said cartridge holder comprises a frame, a clamp and a plunger element containing a piston stem;

said cartridge loaded into the frame of said cartridge holder; and wherein said coupling system for transferring said medicament from said cartridge to said pre-slit injection site comprises: a hub having a flow channel located centrally therein, said flow channel comprising:

a needle cannula having a proximal and distal end and a sharp end at the proximal end of the hub; and a blunt cannula at the distal end of the hub;

said hub comprises:

a first sleeve located on the proximal end of the hub and designed to engage a closure on said medicament-containing cartridge;

a second sleeve located on the distal end of the hub having internal threads thereon to engage said catheter connected to said pre-slit injection site; and a middle portion integral with and connecting the sleeves on the proximal and distal ends of the hub;

said first sleeve covering in a spaced relationship and extending beyond the sharp end of said needle cannula to prevent accidental needle strikes, wherein said cartridge can be advanced distally through said holder by rotating said clamp such that the proximal end of said needle cannula penetrates said diaphragm, and said piston stem can be connected to said piston and actuated to drive said piston through said cartridge and expulse medicament contained in said cartridge through said fluid flow channel into pre-slit injection site.

Embodiment II

In this embodiment of the present invention there is provided a coupling system that is compatible with various pre-slit injection sites. Accordingly, there is provided a coupling system for transferring a medicament from a cartridge to a pre-slit injection site wherein said pre-slit injection site comprises:

a cylindrical housing having a first end and a second end;

internal male luer threads located in said cylindrical housing adjacent to said second end to receive and engage a catheter having female luer threads thereon;

a hollow cylindrical funnel-shaped fluid flow member providing a sterile fluid flow coupling when said catheter is engaged with said pre-slit injection site; said hollow cylindrical funnel-shaped fluid flow member being a female member comprising:

a distal cylindrical end portion;

a middle tapered portion having a taper angle of from about 2° to about 20° to the longitudinal axis of said cylindrical funnel-shaped fluid flow member; and a proximal cylindrical end portion; and a resealable septum located at the first end of said housing to seal said pre-slit injection site when said pre-slit injection site is not engaged by said catheter;

wherein said coupling system comprises:

a hub having a proximal and distal end and a flow channel located centrally therein, said flow channel comprising:

a needle cannula having a sharp end at the proximal end of the hub; and a blunt cannula at the distal end of the hub;

said blunt cannula being a male member comprising:

a distal cylindrical end portion;

a middle tapered portion having a taper angle of from about 2° to about 20° to the longitudinal axis of said blunt cannula; and a proximal cylindrical end portion;

said male member is designed to engage said female member when the coupling system is connected to the injection site;

said hub comprising:

a first sleeve located on the proximal end of the hub and designed to engage a closure on a cartridge;

a second sleeve located on the distal end of the hub having internal threads thereon to engage said catheter connected to said pre-slit injection site; and a middle portion integral with and connecting the sleeves on the proximal and distal ends of the hub;

said first sleeve covering in a spaced relationship and extending beyond the sharp end of said needle cannula.

When the coupling system is used in conjunction with a cartridge, the assembly comprises:

a coupling system for transferring a medicament from a cartridge to a pre-slit injection site wherein said pre-slit injection site comprises:

a cylindrical housing having a first end and a second end;

internal male luer threads located in said cylindrical housing adjacent to said second end to receive and engage a catheter having female luer threads thereon;

a hollow cylindrical funnel-shaped fluid flow member providing a sterile fluid flow coupling when said catheter is engaged with said pre-slit injection site; said hollow cylindrical funnel-shaped fluid flow member being a female member comprising:

a distal cylindrical end portion;

a middle tapered portion having a taper angle of from about 2° to about 20° to the longitudinal axis of said cylindrical funnel-shaped fluid flow member; and a proximal cylindrical end portion; and a resealable septum located at the first end of said housing to seal said pre-slit injection site when said pre-slit injection site is not engaged by said catheter;

wherein said coupling system in combination with a cartridge comprises:

a cartridge, comprising a hollow body prefilled with a medicament having a sealed diaphragm on the distal end thereof and a piston axially and reciprocally slideable through the interior of said body; and a coupling system for transferring said medicament from said cartridge to the pre-slit injection site, said coupling system comprising:

a hub having a proximal and distal end and a flow channel located centrally therein, said flow channel comprising:

a needle cannula having a sharp end at the proximal end of the hub; and a blunt cannula at the distal end of the hub;

said blunt cannula being a male member comprising:

a distal cylindrical end portion;

a middle tapered portion having a taper angle of from about 2° to about 20° to the longitudinal axis of said blunt cannula; and a proximal cylindrical end portion;

said male member is designed to engage said female member when the coupling system is connected to the injection site;

said hub comprises:

a first sleeve located on the proximal end of the hub and designed to engage a closure on said medicament-containing cartridge;

a second sleeve located on the distal end of the hub having internal threads thereon to engage said catheter connected to said pre-slit injection site; and a middle portion integral with and connecting the sleeves on the proximal and distal ends of the hub;

said first sleeve covering in a spaced relationship and extending beyond the sharp end of said needle cannula to prevent accidental needle strike.

The coupling system is also used in combination with a cartridge holder and holder assembly, the combination comprising:

a coupling system for transferring a medicament form a cartridge to a pre-slit injection site in combination with a cartridge and holder assembly, the combination comprising:

(a) a pre-slit injection site;

(b) a cartridge in a cartridge holder; and (c) a coupling system;

wherein said pre-slit injection site comprises:

a cylindrical housing having a first end and a second end;

internal male luer threads located in said cylindrical housing adjacent to said second end to receive and engage a catheter having female luer threads thereon;

a hollow cylindrical funnel-shaped fluid flow member providing a sterile fluid flow coupling when said catheter is engaged with said pre-slit injection site; said hollow cylindrical funnel-shaped fluid flow member being a female member comprising:
a distal cylindrical end portion;
a middle tapered portion having a taper angle of from about 2° to about 20° to the longitudinal axis of said cylindrical funnel-shaped fluid flow member; and a proximal cylindrical end portion; and
a resealable septum located at the first end of said housing to seal said pre-slit injection site when said pre-slit site is not engaged by said catheter;

wherein said cartridge comprises:
a hollow body prefilled with a medicament having a sealed diaphragm on the distal end thereof and a piston axially and reciprocally slideable through the interior of said body; and
said cartridge holder comprises a frame, a clamp and a plunger element containing a piston stem;
said cartridge loaded into the frame of said cartridge holder; and
wherein said coupling system for transferring said medicament from said cartridge to said pre-slit injection site comprises: a hub having a flow channel located centrally therein,
said flow channel comprising:
a needle cannula having a sharp end at the proximal end of the hub; and
a blunt cannula at the distal end of the hub;
said blunt cannula being a male member comprising:
a distal cylindrical end portion;
a middle tapered portion having a taper angle of from about 2° to about 20° to the longitudinal axis of said blunt cannula; and
a proximal cylindrical end portion;
said male member is designed to engage said female member when the coupling system is connected to the injection site;
said hub comprising:
a first sleeve located on the proximal end of the hub and designed to engage a closure on a cartridge;
a second sleeve located on the distal end of the hub having internal threads thereon to engage said catheter connected to said pre-slit injection site; and
a middle portion integral with and connecting the sleeves on the proximal and distal ends of the hub;
said first sleeve covering in a spaced relationship and extending beyond the sharp end of said needle cannula to prevent accidental needle strikes,
wherein said cartridge can be advanced distally through said holder by rotating said clamp such that the proximal end of said needle cannula penetrates said diaphragm, and
said piston stem can be connected to said piston and actuated to drive said piston through said cartridge and expulse the fluid contents of said cartridge through said fluid flow channel into an injection site.

Embodiment III

Embodiment III of the present invention is designed to provide a coupling system having a retention feature which inhibits easy or unintentional removal of the coupling system from a pre-slit injection site.

Accordingly, there is provided a coupling system for transferring a medicament from a cartridge to a pre-slit injection site wherein said pre-slit injection site comprises:
a cylindrical housing having a first end and a second end;
internal male luer threads located in said cylindrical housing adjacent to said second end to receive and engage a catheter having female luer threads thereon;
a hollow cylindrical funnel-shaped fluid flow member providing a sterile fluid flow coupling when said catheter is engaged with said pre-slit injection site; said hollow cylindrical funnel-shaped fluid flow member being a female member comprising:
a distal cylindrical end portion;
a middle tapered portion having a taper angle of from about 2° to about 20° to the longitudinal axis of said cylindrical funnel-shaped fluid flow member; and a proximal cylindrical end portion; and
a resealable septum located at the first end of said housing to seal said pre-slit injection site when said pre-slit site is not engaged by said catheter;

wherein said coupling system comprises:
a hub having a proximal and distal end and a flow channel located centrally therein, said flow channel comprising:
a needle cannula having a sharp end at the proximal end of the hub; and
a blunt cannula at the distal end of the hub;
said blunt cannula being a male member comprising:
a distal cylindrical end portion having a retention button thereon;
a middle tapered portion having a taper angle of from about 2° to about 20° to the longitudinal axis of said blunt cannula; and
a proximal cylindrical end portion;
said male member is designed to engage said female member when the coupling system is connected to the injection site;
said hub comprising:
a first sleeve located on the proximal end of the hub and designed to engage a closure on a cartridge;
a second sleeve located on the distal end of the hub having internal threads thereon to engage said catheter connected to said pre-slit injection site; and
a middle portion integral with and connecting the sleeves on the proximal and distal ends of the hub;
said first sleeve covering in a spaced relationship and extending beyond the sharp end of said needle cannula.

When the coupling system is used in conjunction with a cartridge, the assembly comprises:
a coupling system for transferring a medicament from a cartridge to a pre-slit injection site wherein said pre-slit injection site comprises:
a cylindrical housing having a first end and a second end;
internal male luer threads located in said cylindrical housing adjacent to said second end to receive and engage a catheter having female luer threads thereon;
a hollow cylindrical funnel-shaped fluid flow member providing a sterile fluid flow coupling when said catheter is engaged with said pre-slit injection site; said hollow cylindrical funnel-shaped fluid flow member being a female member comprising:
a distal cylindrical end portion;
a middle tapered portion having a taper angle of from about 2° to about 20° to the longitudinal axis of said cylindrical funnel-shaped fluid flow member; and a proximal cylindrical end portion; and
a resealable septum located at the first end of said housing to seal said pre-slit injection site when said pre-slit injection site is not engaged by said catheter;

wherein said coupling system in combination with a cartridge comprises:
 a cartridge, comprising a hollow body prefilled with a medicament having a sealed diaphragm on the distal end thereof and a piston axially and reciprocally slideable through the interior of said body; and
 a coupling system for transferring said medicament from said cartridge to the pre-slit injection site, said coupling system comprising:
  a hub having a proximal and distal end and a flow channel located centrally therein, said flow channel comprising:
   a needle cannula having a sharp end at the proximal end of the hub; and
   a blunt cannula at the distal end of the hub;
 said blunt cannula being a male member comprising:
  a distal cylindrical end portion having a retention button thereon;
  a middle tapered portion having a taper angle of from about 2° to about 20° to the longitudinal axis of said blunt cannula; and
  a proximal cylindrical end portion;
 said male member is designed to engage said female member when the coupling system is connected to the injection site;
 said hub comprises:
  a first sleeve located on the proximal end of the hub and designed to engage a closure on said medicament-containing cartridge;
  a second sleeve located on the distal end of the hub having internal threads thereon to engage said catheter connected to said pre-slit injection site; and
  a middle portion integral with and connecting the sleeves on the proximal and distal ends of the hub;
 said first sleeve covering in a spaced relationship and extending beyond the sharp end of said needle cannula to prevent accidental needle strike.

The coupling system is also used in combination with a cartridge holder and holder assembly, the combination comprising:
 a coupling system for transferring a medicament form a cartridge to a pre-slit injection site in combination with a cartridge and holder assembly, the combination comprising:
  (a) a pre-slit injection site;
  (b) a cartridge in a cartridge holder; and
  (c) a coupling system;
 wherein said pre-slit injection site comprises:
  a cylindrical housing having a first end and a second end;
  internal male luer threads located in said cylindrical housing adjacent to said second end to receive and engage a catheter having female luer threads thereon;
  a hollow cylindrical funnel-shaped fluid flow member providing a sterile fluid flow coupling when said catheter is engaged with said pre-slit injection site; said hollow cylindrical funnel-shaped fluid flow member being a female member comprising:
   a distal cylindrical end portion;
   a middle tapered portion having a taper angle of from about 2° to about 20° to the longitudinal axis of said cylindrical funnel-shaped fluid flow member; and a proximal cylindrical end portion; and
  a resealable septum located at the first end of said housing to seal said pre-slit injection site when said pre-slit site is not engaged by said catheter;
 wherein said cartridge comprises:
  a hollow body prefilled with a medicament having a sealed diaphragm on the distal end thereof and a piston axially and reciprocally slideable through the interior of said body; and
  said cartridge holder comprises a frame, a damp and a plunger element containing a piston stem;
  said cartridge loaded into the frame of said cartridge holder; and
 wherein said coupling system for transferring said medicament from said cartridge to said pre-slit injection site comprises: a hub having a flow channel located centrally therein,
 said flow channel comprising:
  a needle cannula having a sharp end at the proximal end of the hub; and
  a blunt cannula at the distal end of the hub;
 said blunt cannula being a male member comprising:
  a distal cylindrical end portion having a retention button thereon;
  a middle tapered portion having a taper angle of from about 2° to about 20° to the longitudinal axis of said blunt cannula; and
  a proximal cylindrical end portion;
 said male member is designed to engage said female member when the coupling system is connected to the injection site;
 said hub comprising:
  a first sleeve located on the proximal end of the hub and designed to engage a closure on a cartridge;
  a second sleeve located on the distal end of the hub having internal threads thereon to engage said catheter connected to said pre-slit injection site; and
  a middle portion integral with and connecting the sleeves on the proximal and distal ends of the hub;
 said first sleeve covering in a spaced relationship and extending beyond the sharp end of said needle cannula to prevent accidental needle strikes,
 wherein said cartridge can be advanced distally through said holder by rotating said clamp such that the proximal end of said needle cannula penetrates said diaphragm, and
 said piston stem can be connected to said piston and actuated to drive said piston through said cartridge and expulse the fluid contents of said cartridge through said fluid flow channel into an injection site.

BRIEF DESCRIPTION OF THE DRAWINGS

FIG. 1 is an exploded axial cross-section of the coupling system showing the cannula and hub.

FIG. 2 is an axial cross-section showing the hub taken along the plane defined by 3-3-4-4-3 in FIG. 1.

FIG. 3 is a top plan view of the hub.

FIG. 4 is a bottom plan view of the hub.

FIG. 14 is an exploded axial cross-section of the coupling system showing the cannula and hub.

FIG. 15 is an axial cross-section showing the hub taken along the plane defined by 3-3-4-4-3 in FIG. 14.

FIG. 16 is a top plan view of the hub.

FIG. 17 is a bottom plan view of the hub.

DESCRIPTION OF THE PREFERRED EMBODIMENTS

Figure 5:
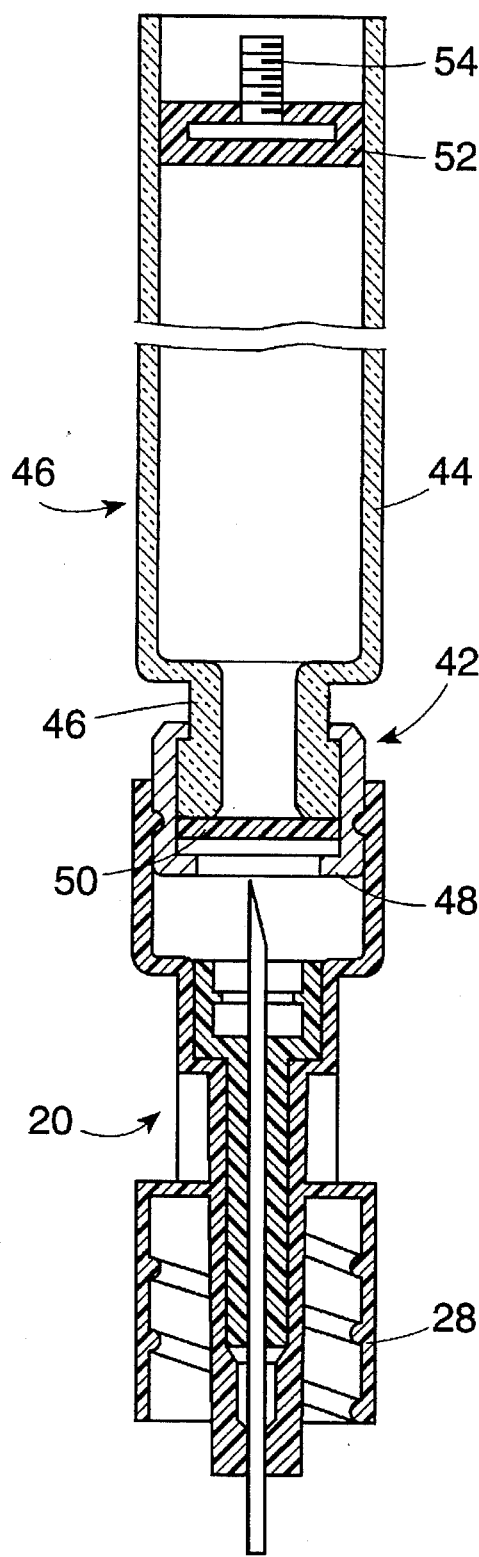
FIG. 5 is a cross-section of the coupling system in combination with a liquid medication-containing cartridge.

While this invention is described hereinafter particularly with respect to preferred embodiments comprising: a coupling system for transferring fluids from a medicament-containing cartridge to a pre-slit injection site, it also finds utility in other coupling systems for transferring fluid materials from one flow conduit to another.

The present invention is described in reference to preferred embodiments I, II and III shown by FIGS. 1–7, FIGS. 8–13 and FIGS. 14–19 respectively.

Embodiment I (FIGS. 1–7)

With reference to the drawings of FIGS. 1–7, the coupling system of Embodiment I of the present invention, represented generally by 10 in FIG. 1, is intended for use in combination with a conventional disposable medicament-containing cartridge. The coupling system includes a fluid flow channel comprising: a blunt cannula 16 defining the distal end of the fluid flow channel, a needle cannula 18 defining the proximal end of the fluid flow channel, and a hub 20 for connecting the needle cannula to the blunt cannula as well as serving other important functions described hereinafter.

As best can be seen in FIGS. 1, 2, 3 and 4, hub 20 comprises: a unitary body having a proximal end 22 in the form of a first sleeve, a distal end 24 in the form of a second sleeve, and middle portion 26 connecting the proximal end and the distal end. Middle portion 26 has an outside diameter which is smaller than the outside diameters of the sleeves on the proximal and distal ends of the hub. Preferably, middle portion 26 is provided with a plurality of parallel ridges 28 connecting the proximal and distal ends of the hub and serve the purposes of reinforcement and facilitating manufacturing. The middle portion 26 of hub 20, having a smaller outside diameter than the outside diameters of the first and second sleeves will snugly fit into the distal end of cartridge holder shown in FIG. 7. However, the larger diameter sleeves will serve as stopping means not allowing the cartridge coupling system to move axially within the cartridge holder.

First sleeve forming the proximal end 22 of hub 20 has an inside diameter which is slightly less or equal to the outside diameter of the closure cap on the cartridge so that the sleeve may be snapped-on the closure cap when assembling the coupling system with the cartridge.

Second sleeve forming the distal end 24 of hub 20 has an inside diameter that is larger than the outside diameter of a receiving means at the pre-slit injection site so as to allow the receiving means to fit inside the second sleeve when the distal end of the coupling system is engaged with the receiving means of the pre-slit injection site. Second sleeve at the distal end 24 of hub 20 is provided with internal threads to allow receiving means to be threaded into said second sleeve thereby forming a tight, leak-proof connection between the respective parts.

A fluid flow channel is provided in the coupling system comprising: the needle cannula 18 and blunt cannula 16. First sleeve 22 extends around and beyond the proximal end 12 of needle cannula 18 when assembled. The assembly of the coupling system at the manufacturer's site virtually eliminates user exposure to accidental needle strikes.

Needle cannula 18 can be a single or double sharp ended needle cannula of the type commonly associated with hypodermic syringes. A needle cannnla of the single ended type, as shown in FIG. 1, is preferred. The needle cannula preferably is fabricated of stainless steel.

Figure 6:
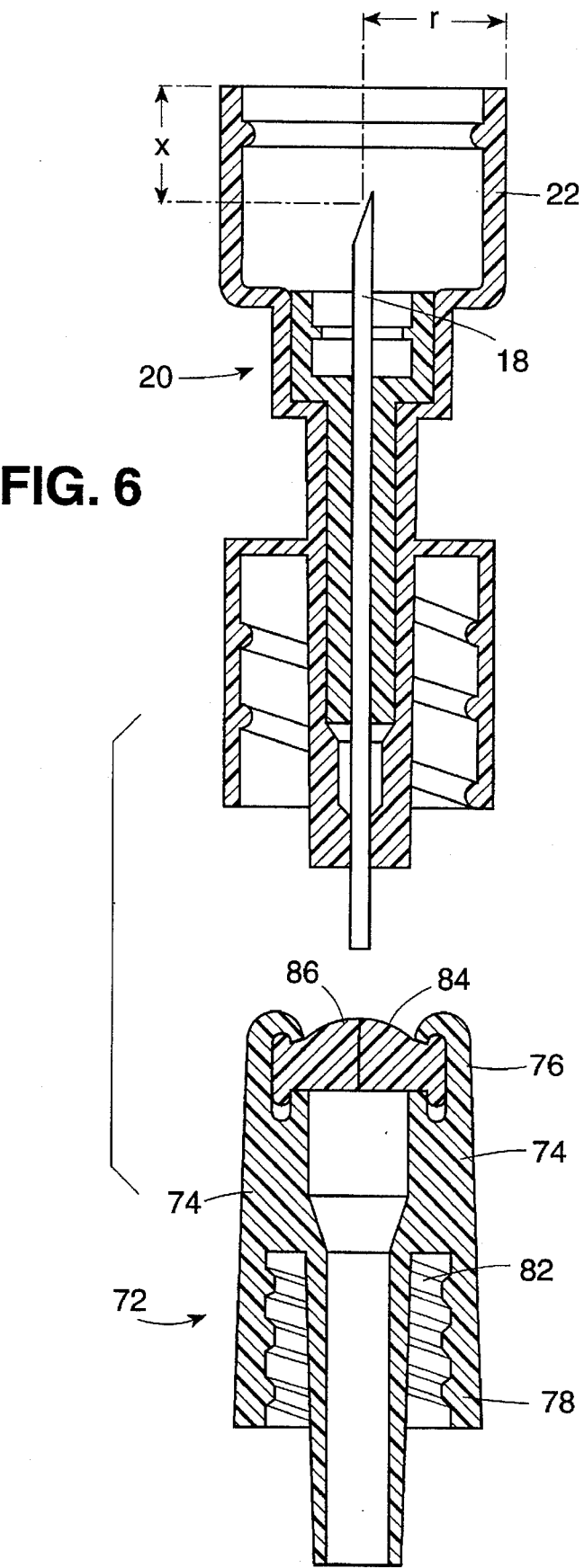
FIG. 6 is a cross-section of the coupling system and a pre-slit injection site.

As shown in FIG. 6, for use with conventional cartridges, e.g., commercially available Carpuject™ sterile cartridges, the radius r of sleeve 22 is about 5 mm and the distance x between the end of sleeve 22 and the proximal end 12 of needle cannula 18 preferably is at least about 2 mm, more preferably 3 mm, so that the proximal end of the needle cannula is adequately shielded when the coupling system is not attached to the cartridge. The distal end of the needle cannula 18 can be flush with the distal end of the blunt cannula. However, to reduce the undesirable possibility of the needle cannula extending beyond the distal end of the blunt cannula due to manufacturing tolerances, a clearance of at least about 0.5 mm, and preferably, of about 1 mm can be provided between the distal end of the needle cannula and the end of the blunt cannula.

Blunt cannula 16 is tapered at its distal end to engage an injection site. The blunt cannula 16 preferably is an integral part of hub 20. The specifics of the design of the tapered blunt cannula end portion of hub 20 can be ascertained with reference to PCT/US89/000273, and PCT/US90/01350, the disclosures of which are hereby incorporated by reference, which describe tapered blunt cannula for use with pre-slit injection sites.

Various means can be employed for fixedly connecting the needle cannula to the blunt cannula and/or the hub comprising the blunt cannula. For example, the fluid flow path inside the blunt cannula can be tapered such that the needle cannula can be inserted into and adhesively connected to the blunt cannula. Suitable adhesives include, e.g., an epoxy based resin, and can be applied to the outside surface of the needle cannula prior to insertion into the hub. Alternatively, the needle cannula can be inserted into the blunt cannula or hub and the blunt cannula or hub can be melted or welded to connect the needle cannula to the blunt cannula.

A removable cover sheath 30 can be provided to surround blunt cannula 16 during storage and handling to preserve the sterility of the cannula. Cover sheath 30 can be snapped into engagement with the hub to surround and protect the outwardly projecting distal end of blunt cannula 16.

Referring to FIG. 5, disposable medication-containing cartridge 40 is of a conventional design and includes a hollow, transparent body which is prefilled with a supply of fluid medication or the like. Such cartridges currently are in widespread commercial use. Cartridge 40 includes a head 42 and a cylindrical body 44 which are coextensively joined together at a relatively narrow neck 46. A metallic end cap 48 covers a sealed diaphragm 50 which extends across cartridge 40 to prevent contamination and leakage of the fluid contents. A piston 52 is sized to be received in and slideable axially and reciprocally through the interior of cartridge 40. Piston 52 is formed from a relatively dense resilient material, e.g., rubber, and can be moved distally through cartridge 40 for expulsing the fluid contents of the cartridge via blunt cannula 16 and needle cannula 18. A screw-threaded red 54 can be connected to the piston 52 so as to project outwardly from the end of piston 52. Screw-threaded rod 54 can be mated to a screw-threaded piston stem of an associated holder to complete a piston assembly for controlling the movement of piston 52 through the interior of cartridge 40. It is contemplated that other means known in the art can be employed for attaching the rod to the piston stem.

Figure 7:
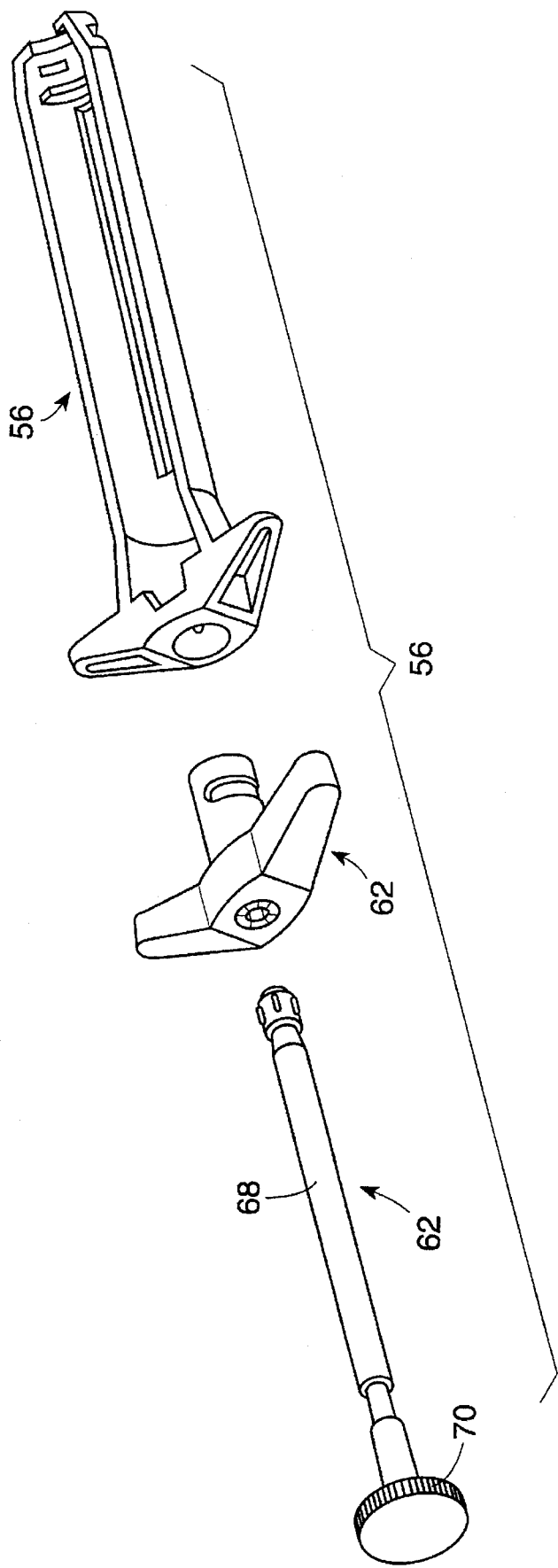
FIG. 7 is an exploded view of a cartridge holder used in conjunction with the coupling system/cartridge combination of the present invention.

The above-described medicament-containing cartridges are designed for use in conjunction with reusable disposable syringe holders. Exemplary useful syringe holders are described, for example, in Hadtke, U.S. Pat. No. 4,585,445 and EPO 485,028 the disclosures of which are hereby incorporated by reference. Such a syringe holder 56 as depicted in FIG. 7, can comprise a cylindrical frame 58, a clamp 60, and a plunger element 62 containing a piston stem 68.

In preferred embodiments, the coupling system of this invention is practiced in conjunction with a pre-slit injection site as described in PCT/US89/00273, PCT/US90/01350 and depicted in FIG. 6. Injection site 72 has a cylindrical housing 74, a first end 76, a second end 78, and a hollow cylindrical fluid flow member 80 which can slideably engage a receiving member, e.g., the housing of a catheter, thereby providing a sterile fluid flow coupling. Internal male luer threads 82, shown to be carried by housing 74 adjacent the second end 78, engage a flange member (not illustrated) when the injection site is rotated. The injection site 72 contains a resealable septum 84 formed of, for example, a latex, synthetic rubber or thermoplastic elastomer. The septum 84 has either a partial or complete opening or slit 86.

The hub 20 preferably is attachable to the cartridge by snapping sleeve portion 22 over the distal end of the cartridge to engage the metal cap 48. In order to obtain the requisite sterile seal and flexibility, the hub preferably is fabricated of a plastic material such as polyethylene or polypropylene, or a polypropylene copolymer containing a minor amount of, e.g., low density polyethylene, to increase the impact strength of the polymer. An example of the latter copolymer is Pro-fax 8523, available from Himont Incorporated. Such copolymer is particularly preferred when the hub is prepared by conventional injection molding techniques.

The coupling system 10 of this invention can be prepared by inserting a needle cannula 18 into hub 20. An adhesive, e.g., a UV curable epoxy resin, can be applied to the needle/insert interface and, subsequently, the resin can be cured. The coupling system 10 preferably is sterilizable such as by means of radiation, steam or ethylene oxide. The needle cannula-insert assembly can then be press fit through the sleeve 22 into the hub 20. The sheath 30 can then be fitted over the hub 20, and the coupling system-sheath assembly can be snap fitted over the necked down end of the cartridge 40.

In use, the coupling system 10 of this invention operates in conjunction with conventional medicament-containing cartridges, reusable syringe holders and injection sites during and after administration of an injection as follows. In the injection state, the prefilled medication cartridge 40 fitted with the coupling system 10 of this invention is loaded into cylindrical frame 58 of an assembled reusable syringe holder 56 such as described above so that blunt cannula 16 covered by sheath 30 extends distally outward from the frame. Cartridge 40 is then advanced by a health care worker distally through the holder by rotating clamping element 60 until the inwardly extending proximal end of needle cannula 12 penetrates sealed diaphragm 50 of cartridge 40.

Next, sheath 30 is removed to expose the outwardly extending distal end of blunt cannula 16. A screw threaded piston stem 68 is connected to piston 52 at the screw-threaded rod 54 thereof. The blunt cannula 16 is inserted into a pre-slit injection site, such as described above. Receiving means is threaded into internally threaded sleeve 24 of hub 20 to tightly hold the coupling system in place. An axially and distally directed force is applied by the health care worker to piston stem 62, via actuation button 70. The distal force is transferred from piston stem 68 to piston 52 to drive the piston through medicament-containing cartridge 40 and thereby expulse the fluid contents of the cartridge 40 via needle cannula 18 through the fluid flow channel and into the fluid flow member 80 of the pre-slit injection site 72. After injection, the blunt cannula 16 is removed from the injection site. Subsequently, the plunger rod 54 is unscrewed from the piston thread and pulled proximally back, the clamp 60 is rotated to free the cartridge 30 and the cartridge unit is disposed of in an appropriate manner, the needle cannula 18 being safely covered by the hub 20, sleeve 22 and/or blunt cannula 16 during the entire procedure, thus reducing the possibility of accidental needle strikes.

Embodiment II (FIGS. 8–13)

Figure 8:
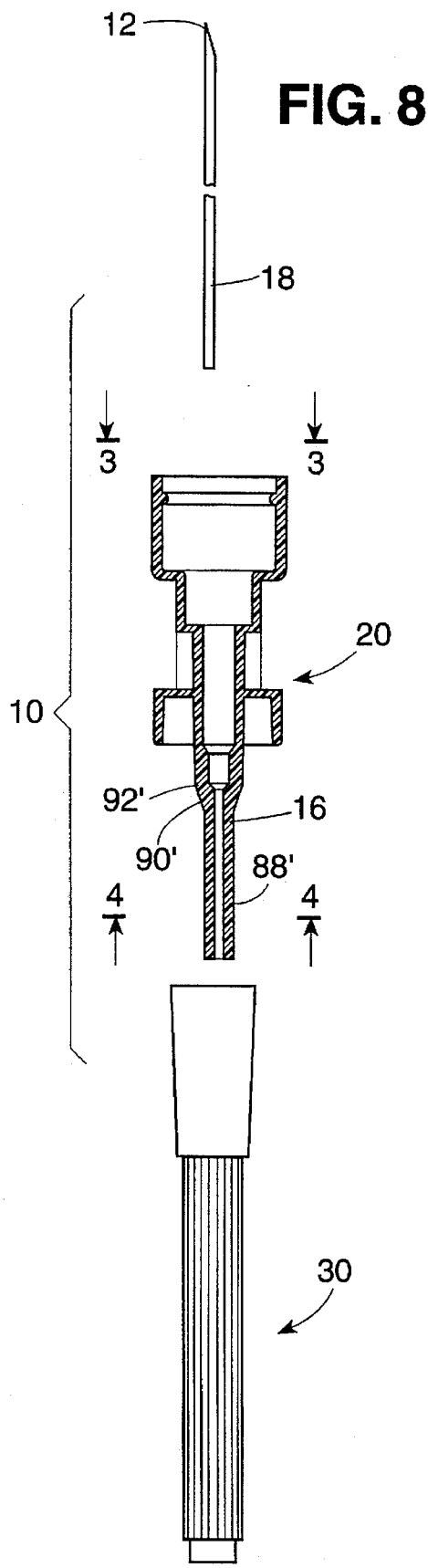
FIG. 8 is an exploded axial cross-section of the coupling system showing the cannula and hub.
Figure 9:
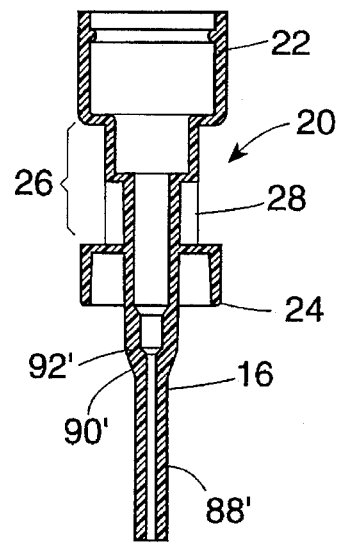
FIG. 9 is an axial cross-section showing the hub taken along the plane defined by 3-3-4-4-3 in FIG. 1.
Figure 10:
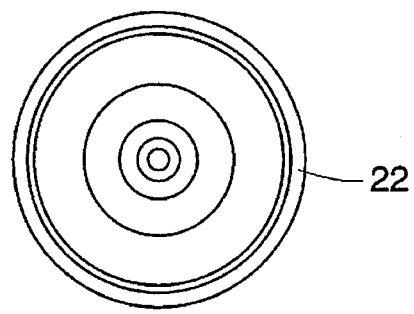
FIG. 10 is a top plan view of the hub.
Figure 11:
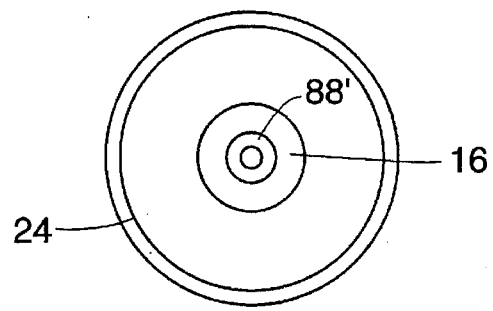
FIG. 11 is a bottom plan view of the hub.

With reference to the drawings of FIGS. 8–13, the coupling system of Embodiment II of the present invention, represented generally by 10 in FIG. 8, is intended for use in combination with a conventional disposable medicament-containing cartridge. The coupling system includes a fluid flow channel comprising: a blunt cannula 16 defining the distal end of the fluid flow channel, a needle cannula 18 defining the proximal end of the fluid flow channel, and a hub 20 for connecting the needle cannula to the blunt cannula as well as serving other important functions described hereinafter.

As shown in FIGS. 8, 9, 10 and 11, hub 20 comprises: a unitary body having a proximal end 22 in the form of a first sleeve, a distal end 24 in the form of a second sleeve, and middle portion 26 connecting the proximal end and the distal end. Middle portion 26 has an outside diameter which is smaller than the outside diameters of the sleeves on the proximal and distal ends of the hub. Preferably, middle portion 26 is provided with a plurality of parallel ridges 28 connecting the proximal and distal ends of the hub and serve the purposes of reinforcement and facilitating manufacturing. The middle portion 26 of hub 20, having a smaller outside diameter than the outside diameters of the first and second sleeves will snugly fit into the distal end of cartridge holder shown in FIG. 7 of Embodiment I. However, the larger diameter sleeves will serve as stopping means not allowing the cartridge coupling system to move axially within the cartridge holder.

First sleeve forming the proximal end 22 of hub 20 has an inside diameter which is slightly less or equal to the outside diameter of the closure cap on the cartridge so that the sleeve may be snapped-on the closure cap when assembling the coupling system with the cartridge.

Second sleeve forming the distal end 24 of hub 20 has an inside diameter that is larger than the outside diameter of a receiving means at the pre-slit injection site so as to allow the receiving means to fit inside the second sleeve when the distal end of the coupling system is engaged with the receiving means of the pre-slit injection site. Second sleeve at the distal end 24 of hub 20 is provided with internal threads to allow receiving means to be threaded into said second sleeve thereby forming a tight, leak-proof connection between the respective parts.

A fluid flow channel is provided in the coupling system comprising: the needle cannula 18 and blunt cannula 16. First sleeve 22 extends around and beyond the proximal end 12 of needle cannula 18 when assembled. The assembly of the coupling system at the manufacturer's site virtually eliminates user exposure to accidental needle strikes.

Needle cannula 18 can be a single or double sharp ended needle cannula of the type commonly associated with hypodermic syringes. A needle cannula of the single ended type, as shown in FIG. 8, is preferred. The needle cannula preferably is fabricated of stainless steel.

Figure 13:
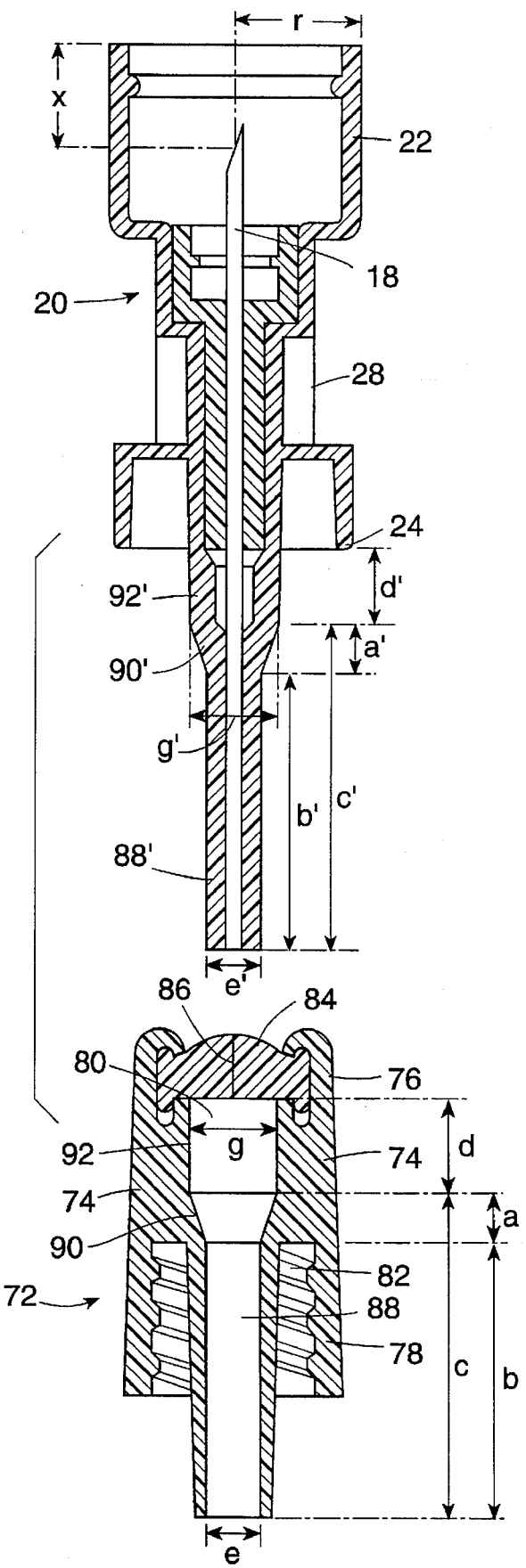
FIG. 13 is a cross-section of the coupling system and a pre-slit injection site.
Figure 18:
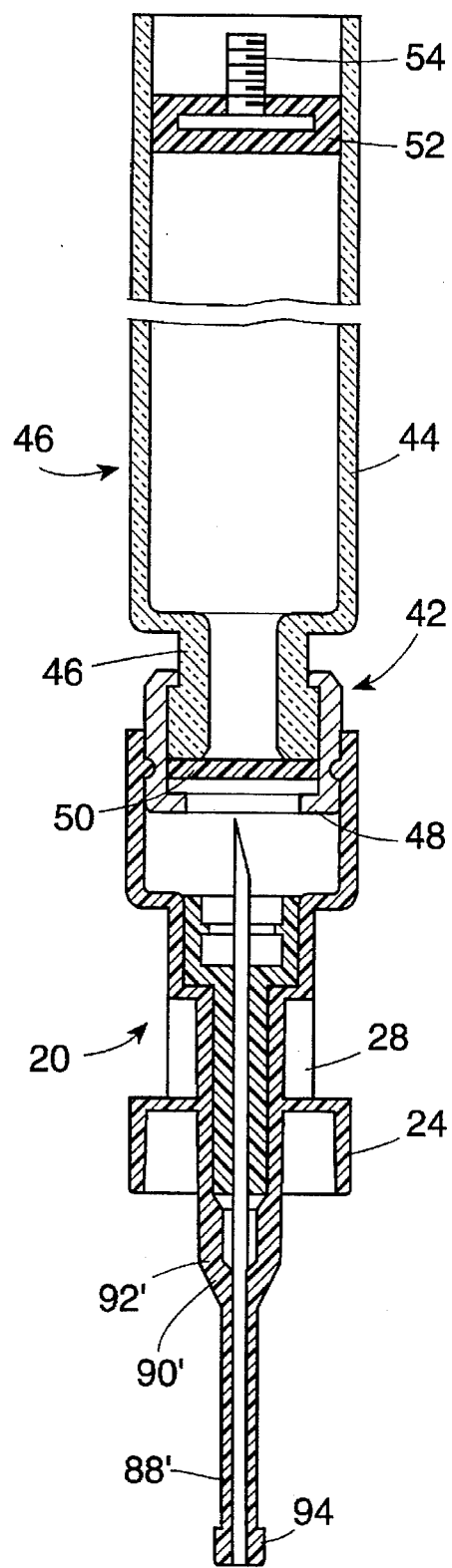
FIG. 18 is a cross -section of the coupling system in combination with a liquid medication-containing cartridge.

As shown in FIG. 13, for use with conventional cartridges, e.g., commercially available Carpuject™ sterile cartridges, the radius r of sleeve 22 is about 5 mm and the distance x between the end of sleeve 22 and the proximal end 12 of needle cannula 18 preferably is at least about 2 mm, more preferably 3 mm, so that the proximal end of the needle cannula is adequately shielded when the coupling system is not attached to the cartridge. The distal end of the needle cannula 18 can be flush with the distal end of the blunt cannula. However, to reduce the undesirable possibility of the needle cannula extending beyond the distal end of the blunt cannula due to manufacturing tolerances, a clearance of at least about 0.5 mm, and preferably, of about 1 mm can be provided between the distal end of the needle cannula and the end of the blunt cannula.

Blunt cannula 16 is tapered at its distal end to engage an injection site. The blunt cannula 16 preferably is an integral part of hub 20. Some of the specifics of the design of the tapered blunt cannula end portion of hub 20 can be ascertained with reference to PCT/US89/000273, and PCT/US90/01350, the disclosures of which are hereby incorporated by reference, which describe tapered blunt cannula for use with pre-slit injection sites. Other specifics will be described hereunder as they relate to one of the objects of the present invention, i.e. to a coupling system that is compatible with various pre-slit injection sites.

Blunt cannula 16 is tapered at the distal end comprising: first portion 88'; second portion 90'; and third portion 92'.

Various means can be employed for fixedly connecting the needle cannula 18 to the blunt cannula 16 and/or the hub 20 comprising the blunt cannula. For example, the fluid flow path inside the blunt cannula can be tapered such that the needle cannula can be inserted into and adhesively connected to the blunt cannula. Suitable adhesives include, e.g., an epoxy based resin, and can be applied to the outside surface of the needle cannula prior to insertion into the hub. Alternatively, the needle cannula can be inserted into the blunt cannula or hub and the blunt cannula or hub can be melted or welded to connect the needle cannula to the blunt cannula.

A removable cover sheath 30 can be provided to surround blunt cannula 16 during storage and handling to preserve the sterility of the cannula. Cover sheath 30 can be snapped into engagement with the hub to surround and protect the outwardly projecting distal end of blunt cannula 16.

Figure 12:
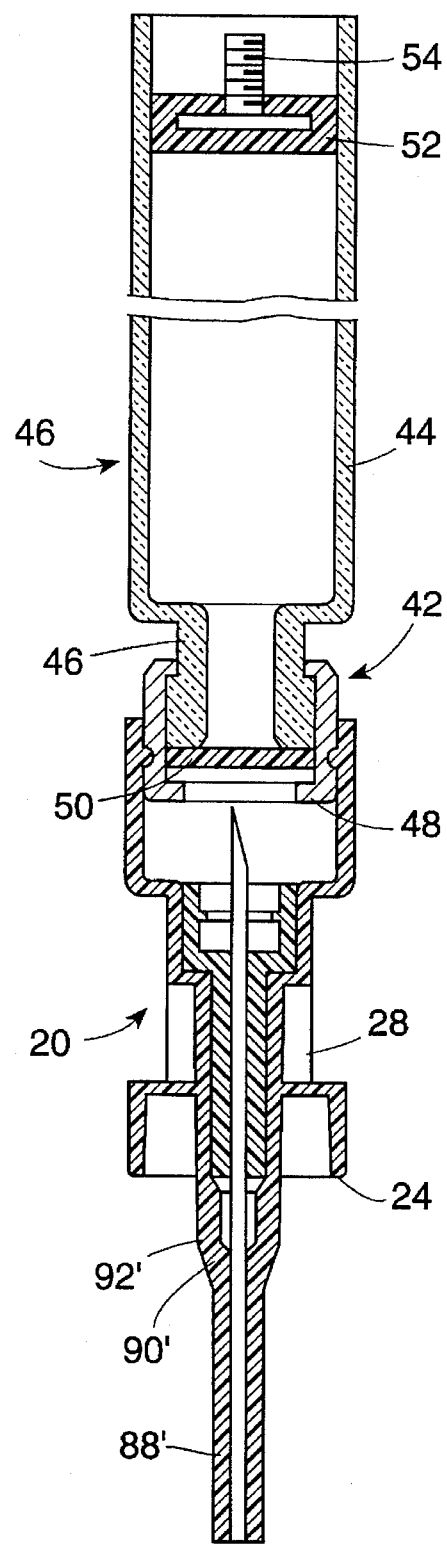
FIG. 12 is a cross-section of the coupling system in combination with a liquid medication-containing cartridge.

Referring to FIG. 12, disposable medication-containing cartridge 40 is of a conventional design and includes a hollow, transparent body which is prefilled with a supply of fluid medication or the like. Such cartridges currently are in widespread commercial use. Cartridge 40 includes a head 42 and a cylindrical body 44 which are coextensively joined together at a relatively narrow neck 46. A metallic end cap 48 covers a sealed diaphragm 50 which extends across cartridge 40 to prevent contamination and leakage of the fluid contents. A piston 52 is sized to be received in and slideable axially and reciprocally through the interior of cartridge 40. Piston 52 is formed from a relatively dense resilient material, e.g., rubber, and can be moved distally through cartridge 40 for expulsing the fluid contents of the cartridge via blunt cannula 16 and needle cannula 18. A screw-threaded rod 54 can be connected to the piston 52 so as to project outwardly from the end of piston 52. Screw-threaded rod 54 can be mated to a screw-threaded piston stem of an associated holder to complete a piston assembly for controlling the movement of piston 52 through the interior of cartridge 40. It is contemplated that other means known in the art can be employed for attaching the rod to the piston stem.

The above-described medicament-containing cartridges are designed for use in conjunction with reusable disposable syringe holders. Exemplary useful syringe holders are described, for example, in Hadtke, U.S. Pat. No. 4,585,445 and EPO 485,028 the disclosures of which are hereby incorporated by reference. Such a syringe holder 56 as depicted in FIG. 7, can comprise a cylindrical frame 58, a clamp 60, and a plunger element 62 containing a piston stem 68.

In this preferred embodiment, the coupling system of the invention is practiced in conjunction with a pre-slit injection site as described in PCT/US89/00273, PCT/US90/01350 and depicted in FIG. 13. Injection site 72 has a cylindrical housing 74, a first end 76, a second end 78, and a hollow cylindrical fluid flow member 80 which can slideably engage a receiving member, e.g., the housing of a catheter, thereby providing a sterile fluid flow coupling. Internal male luer threads 82, shown to be carded by housing 74 adjacent the second end 78, engage a flange member (not illustrated) when the injection site is rotated. The injection site 72 contains a resealable septum 84 formed of, for example, a latex, synthetic rubber or thermoplastic elastomer. The septum 84 has either a partial or complete opening or slit 86.

Funnel-shaped fluid flow member 80 comprises: distal cylindrical end portion 88; middle tapered portion 90; and proximal cylindrical end portion 92.

Distal cylindrical end portion 88 has a length, b, of from about 0.100" to about 0.300" and an inside diameter, e, of form about 0.070" to about 0.100". Middle tapered portion 90 has a length, a, of from about 0.090" to about 0.150" and preferably about 0.125" with a taper angle of form about 2° to about 20°, and preferably of from about 5° to about 15°. Proximal cylindrical end portion 92 has a length, d, of from about 0.18041 to about 0.300" and preferably of about 0.250", and an inside diameter, g, of from about 0.100" to about 0.300". Funnel-shaped fluid flow member 80 will serve as the female portion when engaging blunt cannula, 16, which is the male portion.

Injection site 72 containing funnel-shaped fluid flow member 80 therein is to engage cannula 16 which comprises: distal, cylindrical end portion 88'; middle tapered portion 90'; and proximal cylindrical end portion 92'.

Distal cylindrical end portion 88' has a length, b,' of from about 0.100" to about 0.300" and an outside diameter, e', of from about 0.070" to about 0.100". Middle tapered portion 90' has a length, a', of from about 0.090" to about 0.150" and preferably about 0.125" with a taper angle of from about 2° to about 20°, and preferably of from about 5° to about 15°. Proximal cylindrical end portion 92' has a length, d', of from about 0.180" to about 0.300" and preferably of about 0.250", and an outside diameter, g', of from about 0.100" to about 0.300".

When engaged, distal cylindrical end portion 88' of blunt cannula 16 will fit into distal cylindrical end portion of funnel-shaped fluid flow member 88; middle tapered portion 90' of blunt cannula 16 will fit into middle tapered portion 90 of funnel-shaped fluid flow member; and proximal cylindrical end portion 92' of blunt cannula 16 will fit into proximal cylindrical end portion 92 of funnel-shaped fluid flow member.

The dimensions of the funnel-shaped fluid flow member 80, serving as a female member, and the dimensions of the blunt cannula 16, serving as a male member, are adjusted so that there exists a frictional fit with sufficient conformity to prevent leakage during the practice of the present invention. Thus, the outside diameters of the three portions of the male member may be one or two percent smaller than the inside diameters of the three portions of the female member.

The hub 20 preferably is attachable to the cartridge by snapping sleeve portion 22 over the distal end of the cartridge to engage the metal cap 48. In order to obtain the requisite sterile seal and flexibility, the hub preferably is fabricated of a plastic material such as polyethylene or polypropylene, or a polypropylene copolymer containing a minor amount of, e.g., low density polyethylene, to increase the impact strength of the polymer. An example of the latter copolymer is Pro-fax 8523, available from Himont Incorporated. Such copolymer is particularly preferred when the hub is prepared by conventional injection molding techniques.

The coupling system 10 of this invention can be prepared by inserting a needle cannula 18 into hub 20. An adhesive, e.g., a UV curable epoxy resin, can be applied to the needle/insert interface and, subsequently, the resin can be cured. The coupling system 10 preferably is sterilizable such as by means of radiation, steam or ethylene oxide. The needle cannula-insert assembly can then be press fit through the sleeve 22 into the hub 20. The sheath 30 can then be fitted over the hub 20, and the coupling system-sheath assembly can be snap fitted over the necked down end of the cartridge 40.

In use, the coupling system 10 of this invention operates in conjunction with conventional medicament-containing cartridges, reusable syringe holders and injection sites during and after administration of an injection as follows. In the injection state, the prefilled medication cartridge 40 fitted with the coupling system 10 of this invention is loaded into cylindrical frame 58 of an assembled reusable syringe holder 56 such as described above so that blunt cannula 16 covered by sheath 30 extends distally outward from the frame. Cartridge 40 is then advanced by a health care worker distally through the holder by rotating clamping element 60 until the inwardly extending proximal end of needle cannula 12 penetrates sealed diaphragm 50 of cartridge 40.

Next, sheath 30 is removed to expose the outwardly extending distal end of blunt cannula 16. A screw threaded piston stem 68 is connected to piston 52 at the screw-threaded rod 54 thereof. The blunt cannula 16 is inserted into a pre-slit injection site, such as described above. Receiving means is threaded into internally threaded sleeve 24 of hub 20 to tightly hold the coupling system in place. An axially and distally directed force is applied by the health care worker to piston stem 62, via actuation button 70. The distal force is transferred from piston stem 68 to piston 52 to drive the piston through medicament-containing cartridge 40 and thereby expulse the fluid contents of the cartridge 40 via needle cannula 18 through the fluid flow channel and into the fluid flow member 80 of the pre-slit injection site 72. After injection, the blunt cannula 16 is removed from the injection site. Subsequently, the plunger rod 54 is unscrewed from the piston thread and pulled proximally back, the clamp 60 is rotated to free the cartridge 30 and the cartridge unit is disposed of in an appropriate manner, the needle cannula 18 being safely covered by the hub 20, sleeve 22 and/or blunt cannula 16 during the entire procedure, thus reducing the possibility of accidental needle strikes.

Embodiment III (FIGS. 14–19)

FIGS. 14–19 show Embodiment III of the present invention wherein a retention feature in the form of a button 94 is molded onto the distal cylindrical end portion 88' of blunt cannula 16 which serves to inhibit easy or accidental removal of blunt cannula 16 from injection site 72. The details of this embodiment is analogous to Embodiment II except for retention feature in the form of a button which is described hereunder.

Figure 19:
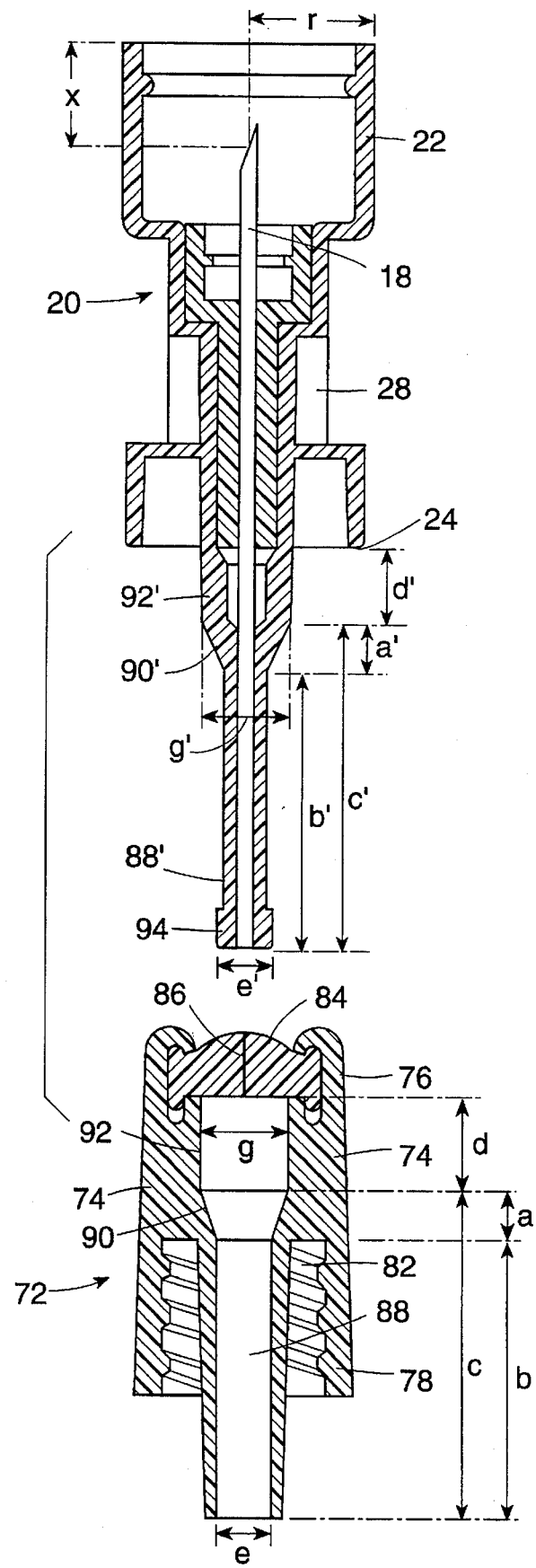
FIG. 19 is a cross-section of the coupling system and a pre-slit injection site.

As best can be seen in FIG. 19, retention button 94 is located at the distal cylindrical end portion 88' of blunt cannula 16 and comprises: length, h, of from about 0.005" to about 0.010" and width, i, of from about 0.005" to about 0.010". Upon insertion of blunt cannula 16 into injection site 72: retention button 94 will fit into distal cylindrical end portion of funnel-shaped fluid flow member 88; middle tapered portion 90' of blunt cannula 16 will fit into middle tapered portion 90 of funnel-shaped fluid flow member; and proximal cylindrical end portion 92' of blunt cannula 16 will fit into proximal cylindrical end portion 92 of funnel-shaped fluid flow member.

Similarly to Embodiment II, the dimensions of the funnel-shaped fluid flow member 80 serving as a female member, and the dimensions of the blunt cannula 16, having retention button 94 thereon, serving as a male member, are adjusted so that there exists a frictional fit with sufficient conformity to prevent leakage during the practice of the present invention.

Retention button 94 prevents easy or accidental removal of blunt cannula 16 from injection site 72: upon an external pulling force exerted upon blunt cannula 16, retention button 94 will contact resealable septum 84 which will prevent further movement of the retention button 94 outward form injection site 72.

The invention has been described in detail with particular reference to certain preferred embodiments thereof, but it will be understood that variations and modifications can be effected within the spirit and scope of the invention.

What is claimed is:

1. A coupling system for transferring a medicament from a cartridge to a pre-slit injection site wherein said pre-slit injection site comprises:

a cylindrical housing having a first end and a second end;
   internal male luer threads located in said cylindrical housing adjacent to said second end to receive and engage a catheter having female luer threads thereon;
   a hollow cylindrical funnel-shaped fluid flow member providing a sterile fluid flow coupling when said catheter is engaged with said pre-slit injection site; said hollow cylindrical funnel-shaped fluid flow member being a female member comprising:
a distal cylindrical end portion;
a middle tapered portion having a taper angle of from about 2° to about 20° to the longitudinal axis of said cylindrical funnel-shaped fluid flow member; and a proximal cylindrical end portion; and
a resealable septum located at the first end of said housing to seal said pre-slit injection site when said pre-slit injection site is not engaged by said catheter;
wherein said coupling system comprises:
a hub having a proximal and distal end and a flow channel located centrally therein,
said flow channel comprising:
a needle cannula having a sharp end at the proximal end of the hub; and
a blunt cannula at the distal end of the hub;
said blunt cannula being a male member comprising:
a distal cylindrical end portion;
a middle tapered portion having a taper angle of from about 2° to about 20° to the longitudinal axis of said blunt cannula; and
a proximal cylindrical end portion;
said male member is designed to engage said female member when the coupling system is connected to the injection site;
said hub comprising:
a first sleeve located on the proximal end of the hub and designed to engage a closure on a cartridge;
a second sleeve located on the distal end of the hub having internal threads thereon to engage said catheter connected to said pre-slit injection site; and
a middle portion integral with and connecting the sleeves on the proximal and distal ends of the hub;
said first sleeve covering in a spaced relationship and extending beyond the sharp end of said needle cannula.

2. A coupling system for transferring a medicament from a cartridge to a pre-slit injection site wherein said pre-slit injection site comprises:
a cylindrical housing having a first end and a second end;
internal male luer threads located in said cylindrical housing adjacent to said second end to receive and engage a catheter having female luer threads thereon;
a hollow cylindrical funnel-shaped fluid flow member providing a sterile fluid flow coupling when said catheter is engaged with said pre-slit injection site; said hollow cylindrical funnel-shaped fluid flow member being a female member comprising:
a distal cylindrical end portion;
a middle tapered portion having a taper angle of from about 2° to about 20° to the longitudinal axis of said cylindrical funnel-shaped fluid flow member; and a proximal cylindrical end portion; and
a resealable septum located at the first end of said housing to seal said pre-slit injection site when said pre-slit injection site is not engaged by said catheter;
wherein said coupling system in combination with a cartridge comprises:
a cartridge, comprising a hollow body prefilled with a medicament having a sealed diaphragm on the distal end thereof and a piston axially and reciprocally slideable through the interior of said body; and
a coupling system for transferring said medicament from said cartridge to the pre-slit injection site, said coupling system comprising:

a hub having a proximal and distal end and a flow channel located centrally therein, said flow channel comprising:
a needle cannnla having a sharp end at the proximal end of the hub; and
a blunt cannula at the distal end of the hub;
said blunt cannula being a male member comprising:
a distal cylindrical end portion;
a middle tapered portion having a taper angle of from about 2° to about 20° to the longitudinal axis of said blunt cannula; and
a proximal cylindrical end portion;
said male member is designed to engage said female member when the coupling system is connected to the injection site;
said hub comprises:
a first sleeve located on the proximal end of the hub and designed to engage a closure on said medicament-containing cartridge;
a second sleeve located on the distal end of the hub having internal threads thereon to engage said catheter connected to said pre-slit injection site; and
a middle portion integral with and connecting the sleeves on the proximal and distal ends of the hub;
said first sleeve covering in a spaced relationship and extending beyond the sharp end of said needle cannula to prevent accidental needle strike.

3. A coupling system for transferring a medicament form a cartridge to a pre-slit injection site in combination with a cartridge and holder assembly, the combination comprising:
(a) a pre-slit injection site;
(b) a cartridge in a cartridge holder; and
(c) a coupling system;
wherein said pre-slit injection site comprises:
a cylindrical housing having a first end and a second end;
internal male luer threads located in said cylindrical housing adjacent to said second end to receive and engage a catheter having female luer threads thereon;
a hollow cylindrical funnel-shaped fluid flow member providing a sterile fluid flow coupling when said catheter is engaged with said pre-slit injection site; said hollow cylindrical funnel-shaped fluid flow member being a female member comprising:
a distal cylindrical end portion;
a middle tapered portion having a taper angle of from about 2° to about 20° to the longitudinal axis of said cylindrical funnel-shaped fluid flow member; and a proximal cylindrical end portion; and
a resealable septum located at the first end of said housing to seal said pre-slit injection site when said pre-slit site is not engaged by said catheter;
wherein said cartridge comprises:
a hollow body prefilled with a medicament having a sealed diaphragm on the distal end thereof and a piston axially and reciprocally slideable through the interior of said body; and
said cartridge holder comprises a frame, a damp and a plunger element containing a piston stem;
said cartridge loaded into the frame of said cartridge holder; and
wherein said coupling system for transferring said medicament from said cartridge to said pre-slit injection site comprises: a hub having a flow channel located centrally therein, said flow channel comprising:
  a needle cannula having a sharp end at the proximal end of the hub; and
  a blunt cannula at the distal end of the hub;
said blunt cannula being a male member comprising:
  a distal cylindrical end portion;
  a middle tapered portion having a taper angle of from about 2° to about 20° to the longitudinal axis of said blunt cannula; and
  a proximal cylindrical end portion;
said male member is designed to engage said female member when the coupling system is connected to the injection site;
said hub comprising:
  a first sleeve located on the proximal end of the hub and designed to engage a closure on a cartridge;
  a second sleeve located on the distal end of the hub having internal threads thereon to engage said catheter connected to said pre-slit injection site; and
  a middle portion integral with and connecting the sleeves on the proximal and distal ends of the hub;
said first sleeve covering in a spaced relationship and extending beyond the sharp end of said needle cannula to prevent accidental needle strikes,
wherein said cartridge can be advanced distally through said holder by rotating said clamp such that the proximal end of said needle cannula penetrates said diaphragm, and
said piston stem can be connected to said piston and actuated to drive said piston through said cartridge and expulse the fluid contents of said cartridge through said fluid flow channel into an injection site.

4. A coupling system for transferring a medicament from a cartridge to a pre-slit injection site wherein said pre-slit injection site comprises:
  a cylindrical housing having a first end and a second end;
  internal male luer threads located in said cylindrical housing adjacent to said second end to receive and engage a catheter having female luer threads thereon;
  a hollow cylindrical funnel-shaped fluid flow member providing a sterile fluid flow coupling when said catheter is engaged with said pre-slit injection site; said hollow cylindrical funnel-shaped fluid flow member being a female member comprising:
    a distal cylindrical end portion;
    a middle tapered portion having a taper angle of from about 2° to about 20° to the longitudinal axis of said cylindrical funnel-shaped fluid flow member; and a proximal cylindrical end portion; and
  a resealable septum located at the first end of said housing to seal said pre-slit injection site when said pre-slit site is not engaged by said catheter;
wherein said coupling system comprises:
  a hub having a proximal and distal end and a flow channel located centrally therein, said flow channel comprising:
    a needle cannula having a sharp end at the proximal end of the hub; and
    a blunt cannula at the distal end of the hub;
    said blunt cannula being a male member comprising:
      a distal cylindrical end portion having a retention button thereon;
      a middle tapered portion having a taper angle of from about 2° to about 20° to the longitudinal axis of said blunt cannula; and
      a proximal cylindrical end portion;
said male member is designed to engage said female member when the coupling system is connected to the injection site;
said hub comprising:
  a first sleeve located on the proximal end of the hub and designed to engage a closure on a cartridge;
  a second sleeve located on the distal end of the hub having internal threads thereon to engage said catheter connected to said pre-slit injection site; and
  a middle portion integral with and connecting the sleeves on the proximal and distal ends of the hub;
said first sleeve covering in a spaced relationship and extending beyond the sharp end of said needle cannula.

5. A coupling system for transferring a medicament from a cartridge to a pre-slit injection site wherein said pre-slit injection site comprises:
  a cylindrical housing having a first end and a second end;
  internal male luer threads located in said cylindrical housing adjacent to said second end to receive and engage a catheter having female luer threads thereon;
  a hollow cylindrical funnel-shaped fluid flow member providing a sterile fluid flow coupling when said catheter is engaged with said pre-slit injection site; said hollow cylindrical funnel-shaped fluid flow member being a female member comprising:
    a distal cylindrical end portion;
    a middle tapered portion having a taper angle of from about 2° to about 20° to the longitudinal axis of said cylindrical funnel-shaped fluid flow member; and a proximal cylindrical end portion; and
  a resealable septum located at the first end of said housing to seal said pre-slit injection site when said pre-slit injection site is not engaged by said catheter;
wherein said coupling system in combination with a cartridge comprises:
  a cartridge, comprising a hollow body prefilled with a medicament having a sealed diaphragm on the distal end thereof and a piston axially and reciprocally slideable through the interior of said body; and
  a coupling system for transferring said medicament from said cartridge to the pre-slit injection site, said coupling system comprising:
    a hub having a proximal and distal end and a flow channel located centrally therein, said flow channel comprising:
      a needle cannula having a sharp end at the proximal end of the hub; and
      a blunt cannula at the distal end of the hub;
      said blunt cannula being a male member comprising:
        a distal cylindrical end portion having a retention button thereon;
        a middle tapered portion having a taper angle of from about 2° to about 20° to the longitudinal axis of said blunt cannula; and
        a proximal cylindrical end portion;
    said male member is designed to engage said female member when the coupling system is connected to the injection site;
    said hub comprises:
      a first sleeve located on the proximal end of the hub and designed to engage a closure on said medicament-containing cartridge;
      a second sleeve located on the distal end of the hub having internal threads thereon to engage said catheter connected to said pre-slit injection site; and a middle portion integral with and connecting the sleeves on the proximal and distal ends of the hub;

said first sleeve covering in a spaced relationship and extending beyond the sharp end of said needle cannula to prevent accidental needle strike.

6. A coupling system for transferring a medicament from a cartridge to a pre-slit injection site in combination with a cartridge and holder assembly, the combination comprising:

(a) a pre-slit injection site;

(b) a cartridge in a cartridge holder; and (c) a coupling system;

wherein said pre-slit injection site comprises:

a cylindrical housing having a first end and a second end;

internal male luer threads located in said cylindrical housing adjacent to said second end to receive and engage a catheter having female luer threads thereon;

a hollow cylindrical funnel-shaped fluid flow member providing a sterile fluid flow coupling when said catheter is engaged with said pre-slit injection site; said hollow cylindrical funnel-shaped fluid flow member being a female member comprising:

a distal cylindrical end portion;

a middle tapered portion having a taper angle of from about 2° to about 20° to the longitudinal axis of said cylindrical funnel-shaped fluid flow member; and a proximal cylindrical end portion; and a resealable septum located at the first end of said housing to seal said pre-slit injection site when said pre-slit site is not engaged by said catheter;

wherein said cartridge comprises:

a hollow body prefilled with a medicament having a sealed diaphragm on the distal end thereof and a piston axially and reciprocally slideable through the interior of said body; and said cartridge holder comprises a frame, a clamp and a plunger element containing a piston stem;

said cartridge loaded into the frame of said cartridge holder; and wherein said coupling system for transferring said medicament from said cartridge to said pre-slit injection site comprises: a hub having a flow channel located centrally therein, said flow channel comprising:

a needle cannula having a sharp end at the proximal end of the hub; and a blunt cannula at the distal end of the hub;

said blunt cannula being a male member comprising:

a distal cylindrical end portion having a retention button thereon;

a middle tapered portion having a taper angle of from about 2° to about 20° to the longitudinal axis of said blunt cannula; and a proximal cylindrical end portion;

said male member is designed to engage said female member when the coupling system is connected to the injection site;

said hub comprising:

a first sleeve located on the proximal end of the hub and designed to engage a closure on a cartridge;

a second sleeve located on the distal end of the hub having internal threads thereon to engage said catheter connected to said pre-slit injection site; and a middle portion integral with and connecting the sleeves on the proximal and distal ends of the hub;

said first sleeve covering in a spaced relationship and extending beyond the sharp end of said needle cannula to prevent accidental needle strikes, wherein said cartridge can be advanced distally through said holder by rotating said clamp such that the proximal end of said needle cannula penetrates said diaphragm, and said piston stem can be connected to said piston and actuated to drive said piston through said cartridge and expulse the fluid contents of said cartridge through said fluid flow channel into an injection site.

* * * * *